United States Patent [19]

Engler

[11] Patent Number: 5,462,727
[45] Date of Patent: Oct. 31, 1995

[54] COMPOSITION FOR INHIBITION OF CORROSION IN GALVANIZED STEEL CANS

[75] Inventor: Steven J. Engler, Coon Rapids, Minn.

[73] Assignee: Dowbrands L.P., Indianapolis, Ind.

[21] Appl. No.: 12,210

[22] Filed: Feb. 2, 1993

[51] Int. Cl.$^6$ .............................. A61K 9/12; C23F 11/00
[52] U.S. Cl. ................. 424/45; 106/14.13; 106/14.15; 424/47
[58] Field of Search .................. 424/45, 47, DIG. 1, 424/DIG. 2, 70, 71; 106/14.13, 14.15

[56] References Cited

U.S. PATENT DOCUMENTS 4,164,562  8/1979  Nandagiri et al. ..................... 424/47
5,085,859  2/1992  Halloran et al. ........................ 424/70

OTHER PUBLICATIONS

Cosmetics & Toiletries, vol. 103, Mar. 1988, p. 115.

*Primary Examiner*—Thurman K. Page

[57] ABSTRACT

Disclosed is a composition for inhibiting corrosion in a galvanized steel can containing an aqueous composition. The composition consists essentially of from about 0.05% to about 5.0% by weight of an alkyl benzoate and from about 0.01% to about 5.0% by weight of an organic borate based on the total weight of the aqueous composition contained in the steel can. Also disclosed is an aqueous hair spray composition contained in a tinplated steel aerosol can, comprising the corrosion inhibiting composition of the invention.

16 Claims, No Drawings

5,462,727

COMPOSITION FOR INHIBITION OF CORROSION IN GALVANIZED STEEL CANS

BACKGROUND OF THE INVENTION

This invention relates to a composition for inhibiting corrosion in galvanized steel cans containing aqueous compositions. More particularly, it relates to a composition for inhibiting corrosion in tinplated steel aerosol cans containing aqueous compositions.

Corrosion of galvanized steel in the presence of water and oxygen is known to occur in galvanized steel cans containing aqueous products. A problem with galvanized steel aerosol cans is that they fail to operate after the corrosion sets in. In extreme cases, corrosion can result in perforation of the aerosol containers with loss of product. Commercially available corrosion inhibitors provide corrosion resistance for short periods of time but are generally not as effective for longer duration.

It would be desirable to provide a composition which, when incorporated in the aqueous composition contained in the galvanized steel cans and particularly in aerosol cans, inhibits crevice corrosion of the cans for longer periods of time than is currently possible.

SUMMARY OF THE INVENTION

In one aspect, the present invention relates to a composition for inhibiting corrosion in a galvanized steel can containing an aqueous composition, consisting essentially of from about 0.05% to about 5.0% of an alkyl benzoate wherein the alkyl group contains 8 to 20 carbon atoms, and from about 0.01% to about 5.0% of an organic borate, based on the total weight of the composition.

In another aspect, the present invention relates to an aqueous hair spray composition contained in a tinplated steel aerosol can, comprising a corrosion inhibiting composition which consists essentially of from about 0.05% to about 5.0% of an alkyl benzoate wherein the alkyl group contains 8 to 20 carbon atoms, and from about 0.01% to about 5.0% of an organic borate, based on the total weight of the composition.

DETAILED DESCRIPTION OF THE INVENTION

Alkyl group in the alkyl benzoate represents a fatty alcohol group containing 8 to 20 carbon atoms. The most preferred alkyl benzoate is an alkyl benzoate with the alkyl group containing 12 to 15 carbon atoms with CTFA designation: C12-15 Alcohols benzoate and is commercially available under the trade name Finsolv TN® from Finetex Inc.

The alkyl benzoate is used in amounts ranging from about 0.05% to about 5.0% by weight of the composition. Most preferably, it is used in amounts of about 0.25% by weight of the composition.

The organic borate useful for the present composition is a mixture of monoethanolamine borate (MEA-borate) and monoisopropanolamine borate (MIPA-borate). This mixture of organic borates is commercially available under the trade name Monacor BE® from Mona Industries, Inc. Monacor BE® is a 50:50 mixture of monoethanolamine borate (MEA-borate) and monoisopropanolamine borate (MIPA-borate). Typically, it is used in the amounts ranging from about 0.01% to about 5.0% by weight of the composition. Most preferably, it is used in amounts of about 0.2% by weight of the composition.

As used herein, "galvanized steel" refers to electroplated steel which is electroplated with metals which are below iron in the activity series.

As used herein, the term "crevice corrosion" refers to corrosion of the crevices that exist in the galvanized steel cans. Points of specific interest are side seam (lap joint), body side wall, double seams at the bottom of the can, and at the clinched juncture.

As used herein, the term "pit corrosion" refers to the formation of holes in the steel due to can corrosion. Pitting is favored at the junctural areas where the metal is stressed or areas poorly protected by tin or by enamel lining (if used).

As used herein, the term "inhibit" refers to suppression, control, stasis, retardation or any other interference with the corrosion process in the galvanized steel can.

Corrosion and detinning of tinplated steel

Most corrosion in metal containers is the result of electrochemical processes. The electrochemical process with different metals is called galvanic action and the electrochemical corrosion is referred to as galvanic corrosion. In electrochemical or galvanic corrosion, the attack on the metal occurs primarily at the anode. A tinplated steel aerosol can is a three layered metal can with a middle layer of an alloy of iron and tin ($FeSn_2$) sandwiched between the two outer layers of tin and iron (steel). There are electromotive differences between the tin, and iron layers. The tin layer is the layer which is in contact with the aqueous composition contained in the tinplated steel can. In the tinplated steel cans, the area of the tin coating is very large compared to that of the iron which is usually exposed to the solution only through minute holes in the tin coating. The aqueous composition contains water, which is an electrolyte containing free ions like hydrogen and hydroxyl ions, and is capable of conducting an electric current. It is believed that when the crevice corrosion takes place in an aerosol can, the tin coating acts as the cathode site and the iron (steel) acts as the anode site. Because of the unfavorable relationship of the large area of the cathode and the small area of the anode, the corrosion will be rapid, and concentrated on the relatively small areas of the iron. This results in pinholing. If the tin is anodic and the iron is cathodic then the tin is attacked initially instead of the iron and generalized detinning occurs rather than pinholing.

At low concentrations of oxygen in tinplated steel aerosol canst the tin is anodic and the iron is cathodic, and detinning occurs. At higher concentrations of oxygen, the tin becomes cathodic and the iron anodic, which promotes corrosion. Corrosion of galvanized steel is presumed to proceed in a similar manner.

Method of Use

The alkyl benzoate and the organic borate are generally mixed in the above stated weight ratios with the aqueous composition to be contained in the galvanized steel can.

The composition of the present invention is particularly useful for inhibiting corrosion in tinplated steel aerosol cans containing hair spray compositions comprising water, alcohol, a hair spray resin, and a propellant. Hithertofore, hair spray compositions have been either non-aqueous or have contained small amounts of water. Hair spray compositions containing large amounts of water are described in copending application Ser. No. 954,545, filed Sep. 3, 1992, which is incorporated herein by reference for its teachings. It has been found that the compositions of the present invention inhibit corrosion of the galvanized steel aerosol cans containing hair spray compositions of application Ser. No. 954,545.

A hair spray composition is prepared by mixing together alcohol, water, hair holding resin, neutralizing base if carboxylic group containing resin is used, Monacor BE® (a mixture of MEA-borate and MIPA-borate), Finsolv TN® (C12-15 alcohol benzoate) and optional ingredients such as fragrance, proteins, plasticizers, surface tension reducers, colorants and the like. The above prepared liquid phase is placed in a galvanized steel aerosol container. An aerosol valve is then crimped on to the container and the container pressurized by introducing a propellant into the container.

The mixture of water and alcohol in the hair spray composition functions as a hydroalcoholic carrier for the hair holding resin.

The essential ingredients in the hair spray compositions are described below.

Hair Holding Resin

Any ionic resin soluble both in water and a lower aliphatic alcohol may be used as a hair holding ingredient. Suitable commercially available resins include polyvinylpyrrolidone or polymeric materials containing one or more carboxylic group. The carboxylic group containing polymeric material is selected from the group consisting of monoethylester of poly(methyl vinyl ether maleic acid); copolymers of polyvinylpyrrolidone and vinyl acetate; polyvinyl alcohol and crotonic acid; polyvinylacetate and maleic anhydride; octylacrylamide/acrylate and butylaminoethyl methacrylate; polyvinylpyrrolidone, ethylmethacrylate and methacrylic acid; vinyl acetate; crotonic acid and vinyl neodecanoate.

The amount of the resin used varies from about 1% to about 10% by weight of the composition. Preferably, the amount of resin used is about 3.0% by weight of the composition.

When a carboxylic group containing resin is used, the free carboxylic groups are partially or completely neutralized by addition of an organic base in the amounts from about 0.2% to about 2% by weight of the composition. Suitable bases include monoethanolamine, diethanolamine, triethanolamine, 2-amino-2-methy-1-propanol, and the like. The most suitable organic base is 2-amino-2-methy-1-propanol used in an amount of about 0.5% by weight of the composition.

Hydroalcoholic carrier

The hydroalcoholic carrier for the hair holding resin comprises water in amounts from about 5% to about 27% by weight of the composition, and at least one aliphatic alcohol containing 1-4 carbon atoms. The weight percent of the aliphatic alcohol is not critical. It is added in amounts sufficient to make up 100% of the composition after desired weight percents of the essential and optional ingredients are added.

Suitably, the water may be soft, deionized, purified or distilled water. It is preferred that deionized water is used. The alcohol may preferably be an anhydrous ethanol or 190-proof ethanol.

Propellant

A propellant is essential for expelling the liquid phase from the aerosol container. The propellant gas can be any liquefiable gas conventionally used for aerosol containers. Suitable materials include lower aliphatic hydrocarbons containing 1–5 carbon atoms, used singly or as mixtures. The amount of the propellant used varies from about 5% to about 18% by weight of the total composition.

Crevice corrosion of the tinplated steel aerosol can containing aqueous composition is determined by Crevice Corrosion test described below.

Crevice Corrosion Test

Crevice Corrosion Test, standardized by United States Can Company, is used to determine the efficacy of various corrosion inhibiting test compositions towards crevice corrosion and detinning.

An enamel coated tinplated steel plate (blank plate) measuring 8×8 inches is scratched by making two parallel scratches, about one centimeter apart, through the coatings. Two similar scratches are made perpendicular to the first two scratches.

A glass cylinder with both ends open with one open end adapted to be clamped onto the blank sheet is sealed against the blank plate at the one open end by means of an O ring. A total of 8 crevice sites are thus established at the juncture of the O ring with the scratches on the blank plate. This is the test cell.

The test cell is filled with the compositions of the Examples described hereinbelow to a height of about one and a half inches. A rubber stopper with a graphite electrode passing through it is placed at the other open end of the cylinder with the electrode partially immersed in the compositions.

The graphite electrode and the composition are joined with a wire to promote galvanic corrosion on the crevice sites covered by the compositions. The test is run for about 72 hours. Evaluation of the crevice sites for crevice corrosion is done with a stereo-microscope. The scratches away from the crevice sites are examined for pit corrosion.

Stability

Stability of the aerosol cans with respect to corrosion is determined by observing for crevice corrosion and detinning at the side seams, body walls, bottom seam and for leaks which could ultimately develop due to corrosion in the aerosol can containing aqueous composition. Stabilities are determined at 45° C. after a period of at least three months.

The following Examples are provided to illustrate the invention. The stated amounts are expressed in weight percents unless otherwise indicated.

EXAMPLES 1–5

The hair spray compositions of Examples 1–5 were prepared in the above described manner and filled in tinplated steel aerosol cans. The cans were tested for crevice corrosion, detinning, and stability as described above. The control composition did not contain any corrosion inhibiting agent. The composition of Example 1 contained the composition of the invention, and composition of Example 2 contained only the C12-15 alcohols benzoate. The composition of Example 3 contained Monacor BE® which is known to resist rust in iron and steel cans, but not the corrosion of galvanized steel or tinplated steel. The compositions of Examples 4, and 5 contained corrosion inhibiting agents known in the art.

| Ingredients | Weight percent | | | | | |
|---|---|---|---|---|---|---|
| | Control | 1 | 2 | 3 | 4 | 5 |
| Ethanol (200 proof) | 65.00 | 65.00 | 65.00 | 65.00 | 65.00 | 65.00 |
| Vinyl Acetate/Crotonic acid/Vinyl Neodecanoate Copolymer | 3.00 | 3.00 | 3.00 | 3.00 | 3.00 | 3.00 |
| 2-amino-2-methyl-1-propanol | 0.53 | 0.53 | 0.53 | 0.53 | 0.53 | 0.53 |
| Water | 16.37 | 15.92 | 16.12 | 16.17 | 16.17 | 16.17 |
| Fragrance | 0.10 | 0.10 | 0.10 | 0.10 | 0.10 | 0.10 |
| Hydrocarbon A-70 (Propane/n-Butane) | 15.00 | 15.00 | 15.00 | 15.00 | 15.00 | 15.00 |
| C12–15 Alcohols Benzoate | — | 0.25 | 0.25 | — | — | — |
| MEA-BORATE/MIPA-BORATE | — | 0.20 | — | 0.20 | — | — |
| Sodium nitrite | — | — | — | — | 0.20 | — |
| Sodium Benzoate | — | — | — | — | — | 0.20 |

The Crevice Corrosion Test and determination of detinning of the tinplated steel aerosol cans was done at 8 crevice sites after 72 hours. The stabilities of the cans were determined by looking for corrosion and/or leaks detinning at the side walls, side seam, bottom seam, and at sites where side wall meets bottom seam. The stability of cans towards crevice corrosion was determined after the cans were maintained at 45° C. for three months. The cans were then classified as fail, pass, or of questionable long term stability. The results are reported in Table 1 set forth hereinbelow.

TABLE 1

| | Control | 1 | 2 | 3 | 4 | 5 |
|---|---|---|---|---|---|---|
| Crevice corrosion | at all 8 sites | none | at 4 sites | 1 site | 2 sites | 3 sites |
| Detinning | at all 8 sites | none | at 4 sites | 2 sites minor | 1 site | 2 sites |
| Stability body side wall | corrosion and detinning | none | slight detinning | very slight detinning | very slight detinning | very slight detinning |
| side seams | corrosion and detinning | none | — | — | detinning | detinning |
| bottom seam crevice corrosion | corrosion and detinning | none | slight detinning | some detinning | corrosion & detinning | corrosion & detinning |
| Rating of the can | Fail* | Pass | questionable for longer than 3 months | may corroode on long term | questionable may fail long term | may fail long term |

*means the can leaks

The results in Table 1 indicate that the composition of Example 1 containing the composition of the invention is the most suitable composition providing long lasting stability towards crevice corrosion. The composition of Example 3 provides the desired inhibition towards the crevice corrosion, and detinning for at least three months and may provide stability towards crevice corrosion for even longer periods of time. The control composition without corrosion inhibiting composition failed the test. Compositions 4, and 5 containing commercially known corrosion inhibiting agents yield undesirable results for crevice corrosion, detinning and stability.

What is claimed is:

1. A composition for inhibiting corrosion in a galvanized steel can containing an aqueous composition, consisting essentially of from about 0.05% to about 5.0% of an alkyl benzoate wherein the alkyl group contains 8 to 20 carbon atoms, and from about 0.01% to about 5.0% of an organic borate, based on the total weight of the composition.

2. An aqueous hair spray composition contained in a tinplated steel aerosol can comprising a corrosion inhibiting composition, which consists essentially of from about 0.05% to about 5.0% of an alkyl benzoate wherein the alkyl group contains 8 to 20 carbon atoms, and from about 0.01% to about 5.0% of an organic borate, based on the total weight of the composition.

3. The hair composition of claim 2, wherein the organic borate is a 50:50 mixture of monoethanolamine borate and monoisopropanolamine borate.

4. The hair compositions of claim 3, wherein the alkyl benzoate is C12-15 alcohols benzoate.

5. The hair spray composition of claim 4 further comprising a vapor phase containing from about 5% to about 25% by weight of a propellant and a liquid phase comprising from about 5% to about 27% by weight of water, from about 1% to about 10% by weight of a hair holding resin, and at least one aliphatic alcohol containing 1–4 carbon atoms, in amounts sufficient to total 100% of the composition.

6. The hair spray composition of claim 5, wherein the weight percent of the alkyl benzoate is about 0.25% and the weight percent of the organic borate is about 0.2%, based on the total weight of the composition.

7. The hair spray composition of claim 6, wherein the hair setting resin is polyvinylpyrrolidone or a polymeric material containing a carboxylic group.

8. The hair spray composition of claim 7, wherein the carboxylic group containing polymeric material is selected from the group consisting of monoethylester of poly(methyl vinyl ether maleic acid); copolymers of polyvinylpyrrolidone and vinyl acetate; polyvinyl alcohol and crotonic acid; polyvinylacetate and maleic anhydride; octylacrylamide/acrylate and butylaminoethyl methacrylate; polyvinylpyrrolidone, ethylmethacrylate and methacrylic acid; vinyl acetate, crotonic acid and vinyl neodecanoate.

9. The hair spray composition of claim 8 further comprising an organic base neutralizer for the carboxylic group containing polymeric material.

10. The hair spray composition of claim 9, wherein the organic base is selected from the group consisting of monoethanolamine, diethanolamine, triethanolamine, and 2-amino-2-methy-1-propanol.

11. The hair spray composition of claim 10, wherein the carboxylic group containing polymeric material is a copolymer of vinyl acetate, crotonic acid and vinyl neodecanoate.

12. The hair spray composition of claim 11, wherein the organic base is 2-amino-2-methyl-1-propanol.

13. The hair spray composition of claim 12, wherein the total weight percent of water and the propellant is from about 20% to about 32% of the weight of the composition.

14. The hair spray composition of claim 13, wherein the propellant is selected from a group consisting of mixtures of propane and n-butane, propane and isobutane, and propane, n-butane, and iso-butane.

15. The hair spray composition of claim 14, wherein the vapor pressure of the composition is from about 40 psig to about 70 psig at 70° F.

16. The hair spray composition of claim 14, wherein the vapor pressure of the composition is from about 50 psig to about 70 psig at 70° F.

* * * * *